(12) United States Patent
Park et al.

(10) Patent No.: US 11,016,009 B2
(45) Date of Patent: *May 25, 2021

(54) METHOD FOR ISOLATING EXTRACELLULAR VESICLES USING AQUEOUS TWO-PHASE SYSTEM

(71) Applicants: POSTECH ACADEMY-INDUSTRY FOUNDATION, Pohang-si (KR); THE REGENTS OF THE UNIVERSITY OF MICHIGAN, Ann Arbor, MI (US)

(72) Inventors: Jae Sung Park, Pohang-si (KR); Joseph M Labuz, Ann Arbor, MI (US); Shuichi Takayama, Ann Arbor, MI (US); Hyun Woo Shin, Busan (KR); Chung Min Han, Pohang-si (KR)

(73) Assignees: POSTECH ACADEMY-INDUSTRY FOUNDATION, Pohang-si (KR); THE REGENTS OF THE UNIVERSITY OF MICHIGEN, Ann Arbor, MI (US)

( * ) Notice: Subject to any disclaimer, the term of this patent is extended or adjusted under 35 U.S.C. 154(b) by 707 days.

This patent is subject to a terminal disclaimer.

(21) Appl. No.: 15/562,549

(22) PCT Filed: Mar. 3, 2016

(86) PCT No.: PCT/KR2016/002133
§ 371 (c)(1),
(2) Date: Feb. 27, 2018

(87) PCT Pub. No.: WO2016/159520
PCT Pub. Date: Oct. 6, 2016

(65) Prior Publication Data
US 2018/0164197 A1 Jun. 14, 2018

(30) Foreign Application Priority Data
Mar. 31, 2015 (KR) .................. 10-2015-0045070

(51) Int. Cl.
| G01N 1/40 | (2006.01) |
| C12M 1/26 | (2006.01) |
| C12Q 1/24 | (2006.01) |
| C12Q 1/68 | (2018.01) |
| G01N 33/53 | (2006.01) |
| A61K 35/12 | (2015.01) |
| B01D 17/02 | (2006.01) |
| C12Q 1/6806 | (2018.01) |

(52) U.S. Cl.
CPC .............. G01N 1/40 (2013.01); A61K 35/12 (2013.01); B01D 17/0217 (2013.01); C12M 1/26 (2013.01); C12Q 1/24 (2013.01); C12Q 1/68 (2013.01); C12Q 1/6806 (2013.01); G01N 33/5306 (2013.01)

(58) Field of Classification Search
CPC ..... G01N 1/40; C12Q 1/24; C12Q 1/68; C12Q 1/6806
See application file for complete search history.

(56) References Cited

U.S. PATENT DOCUMENTS

| 2012/0010390 A1* | 1/2012 | Van Alstine | ............. C07K 1/36 530/388.1 |
| 2013/0177595 A1* | 7/2013 | Gho | ....................... A61K 47/10 424/277.1 |
| 2013/0273544 A1 | 10/2013 | Vlassov et al. | |

FOREIGN PATENT DOCUMENTS

| KR | 10-0194075 | 6/1999 |
| KR | 10-0836171 | 6/2008 |
| KR | 10-0863466 | 10/2008 |
| KR | 10-2014-0118524 | 10/2014 |

OTHER PUBLICATIONS

EPO, Supplementary European Search Report of Application No. 16773301.3, dated Oct. 11, 2018.
Shin et al.,"Cancer-derived Extracellular Vesicle Isolation by Aqueous Two-Phase System", Abstract From the Third International Meeting of ISEV 2014. Journal of Extracellular Vesicles. vol. 3. p. 96. XP055317839, May 1, 2014.
Morre D. M et al., "Aqueous two-phase partition applied to the isolation of plasma membranes and Golgi apparatus from cultured mammalian cells", Journal of Chromatography B. vol. 743. No. 1-2, pp. 377-387, Jun. 23, 2000.

(Continued)

*Primary Examiner* — Jezia Riley
(74) *Attorney, Agent, or Firm* — Lex IP Meister, PLLC

(57) ABSTRACT

Disclosed is a method of isolating extracellular vesicles using an aqueous two-phase system (ATPS), including (a) preparing an ATPS by mixing a first material and a second material, which are immiscible with each other, with a body fluid or an aqueous solution containing extracellular vesicles and (b) isolating extracellular vesicles concentrated in the second material of the ATPS. This method can exhibit very high isolation efficiency, a simple isolation manner, and a very short isolation time. The isolation of extracellular vesicles using the ATPS requires no ultracentrifuge and achieves almost 100% isolation efficiency within a short time of about 10~20 min, and thus the method of the invention is practical, is economical due to low costs thereof, can increase the purity of extracellular vesicles contaminated with protein, enables the diagnosis of disease using the isolated extracellular vesicles, and can be applied to various fields using extracellular vesicles.

10 Claims, 14 Drawing Sheets

(56) References Cited

OTHER PUBLICATIONS

Jens Schindler et al., "Aqueous polymer two-phase systems: Effective tools for plasma membrane proteomics". Proteomics. vol. 6. No. 20., pp. 5409-5417, Oct. 1, 2006.

Lu M. et al., "Partitioning of proteins and thylakoid membrane vesicles in aqueous two-phase systems with hydrophobically modified dextran", Journal of Chromatography A., vol. 668. No. 1., pp. 215-228, May 6, 1994.

H. Shin et at., "Cancer-derived Extracellular Vesicle Isolation by Aqueous Two-Phase System", Abstract from the Third International Meeting of ISEV 2014, Journal of Extracellular Vesicles, vol. 3, Article 24214, Poster No. 09A-346, pp. 120, (2014).

D.M. Morre et al., "Aqueous Two-Phase Partition Applied to the Isolation of Plasma Membranes and Golgi Apparatus from Cultured Mammalian Cells", Journal of Chromatography B, Vol. 743, pp. 377-387 (2000).

\* cited by examiner

METHOD FOR ISOLATING EXTRACELLULAR VESICLES USING AQUEOUS TWO-PHASE SYSTEM

GOVERNMENT LICENSE RIGHTS

This invention was made with government support under grant EB005582 awarded by the U.S. National Institutes of Health. The government has certain rights in the invention.

TECHNICAL FIELD

The present invention relates to a method of isolating extracellular vesicles using an aqueous two-phase system, and more particularly to a method of isolating extracellular vesicles using an aqueous two-phase system, which is used to rapidly isolate extracellular vesicles within a short time and also to increase the purity of extracellular vesicles contaminated with protein.

BACKGROUND ART

Extracellular vesicles include exosomes or microvesicles, having a size of about 50 to 1000 nm, and are thus useful as markers for diagnosing disease because they retain the characteristics of original cells.

Conventional techniques for isolating extracellular vesicles include ultracentrifugation isolation, size exclusion, immunoaffinity isolation, a microfluidics chip method, and a polymeric method. Among these, the ultracentrifugation isolation method is widely employed in the isolation of extracellular vesicles and is regarded as the most reliable by virtue of the simple principle therefor.

However, the case where extracellular vesicles are isolated using ultracentrifugation isolation is problematic in that the yield of extracellular vesicles is low, the isolation time thereof is long, and expensive equipment is required therefor.

The size exclusion method, which is mostly used together with the ultracentrifugation isolation method, is advantageous in terms of increasing the purity of extracellular vesicles in a simple manner, but suffers from low yield after isolation because the extracellular vesicles stick to the filter.

The immunoaffinity isolation method enables the isolation of extracellular vesicles at very high specificity by attaching an antibody thereto, but is unsuitable for practical diagnosis because the process of preparing the antibody requires a long period of time and incurs high costs.

With the goal of overcoming the problems with conventional techniques, the present inventors have disclosed Korean Patent Application Publication No. 2014-0050465 regarding a microfluidic chip for isolating extracellular vesicles. The above patent is economically advantageous because extracellular vesicles are isolated from serum using an antibody-coated microfluidic chip, thus enabling extracellular vesicles to be isolated quickly and obviating the need for laboratories, but is disadvantageous in terms of low yield, and hence, there are still problems to be solved so as to be suitable for use in practical and economical diagnosis methods.

Meanwhile, the polymeric method decreases the solubility of body fluids to thereby precipitate extracellular vesicles, but requires a long incubation time, and moreover, protein is precipitated therewith, thus resulting in low precipitate purity, making this method unsuitable for use in diagnosis.

DISCLOSURE

Technical Problem

Accordingly, the present invention is intended to provide a method of isolating extracellular vesicles using an aqueous two-phase system, in which extracellular vesicles may be rapidly isolated from a body fluid at high purity within a short time compared to conventional techniques.

More specifically, conventional techniques for isolating extracellular vesicles have problems such as low yield and impurity contamination, and therefore, the present invention discloses a novel method of isolating extracellular vesicles using an aqueous two-phase system, unlike conventional techniques. The aqueous two-phase system enables the effective separation of different kinds of particles within a short time and is thus frequently utilized for the separation of particles, but research into the isolation of extracellular vesicles using the aqueous two-phase system has not yet been reported.

An objective of the present invention is to provide a method of isolating extracellular vesicles using an aqueous two-phase system, thus achieving rapid isolation at high yield and specificity within a short time.

However, the objectives of the present invention are not limited to the foregoing, and other objectives not disclosed herein will be able to be readily understood by those skilled in the art through the following description.

Technical Solution

The present invention provides a method of isolating extracellular vesicles using an aqueous two-phase system, comprising the steps of: (a) preparing an aqueous two-phase system by mixing a first material and a second material, which are immiscible with each other, with a body fluid or an aqueous solution containing extracellular vesicles; and (b) isolating the extracellular vesicles concentrated at a phase boundary between the first material and the second material of the aqueous two-phase system or in the second material of the aqueous two-phase system. Here, the method of the invention may further comprise, after the step (a), adding an additive to thus control Van der Waals interaction, hydrogen bonding, hydration, hydrophobic interaction or electrostatic interaction, and centrifuging the aqueous two-phase system at 100~5,000×g-force.

The first material/second material, which constitute the aqueous two-phase system, may be selected from among water/EOPO (ethylene oxide propylene oxide), polyethylene glycol/dextran, polyethylene glycol/high-concentration salt, polyethylene glycol/levan, polyvinyl pyrrolidone/dextran, polyvinyl alcohol/dextran, ficoll/dextran, polyethylene glycol/poly(vinyl methyl ethyl ether), polyethylene glycol/ammonium sulfate, polyethylene glycol/sodium sulfate, polyethylene glycol/magnesium sulfate, polyethylene glycol/potassium phosphate, and polyethylene glycol/sodium carbonate.

When the first material is polyethylene glycol and the second material is dextran, the polyethylene glycol preferably has a molecular weight of 0.2~600 kDa and a concentration of 1~20 wt %, and the dextran preferably has a molecular weight of 15~2,000 kDa and a concentration of 1~20 wt %.

The purity of extracellular vesicles contaminated with protein may be increased using the above method of the invention, and the extracellular vesicles are preferably at least one selected from the group consisting of exosomes, microvesicles, and microparticles. Also, assay such as ELISA, PCR, western blot, proteomics, or genomics may be performed using the vesicles thus isolated.

The present invention provides an apparatus for isolating extracellular vesicles using an aqueous two-phase system, comprising: an inlet 10, configured to introduce a first material and a second material, which constitute an aqueous two-phase system; a feeder 20, configured to feed a body fluid or an aqueous solution containing extracellular vesicles; a main body 30, connected to the inlet and the feeder and configured to isolate extracellular vesicles by mixing and centrifuging the body fluid or the aqueous solution containing extracellular vesicles, the first material and the second material; and a collector 40, configured to recover the isolated extracellular vesicles from the main body 30.

The inlet 10 may include a first inlet 10a for introducing the first material and a second inlet 10b for introducing the second material, and a mixer 50 may be further disposed between the inlet 10 and the feeder 20 so as to mix the body fluid or the aqueous solution containing extracellular vesicles with the first material and the second material. As such, the mixer 50 is preferably equipped with a vibrator, and the main body 30 preferably has a cylindrical shape or a gourd shape.

Advantageous Effects

According to the present invention, a method of isolating extracellular vesicles using an aqueous two-phase system can exhibit very high isolation efficiency, a simple isolation process, and a very short isolation time compared to conventional techniques. More specifically, the isolation of extracellular vesicles using an aqueous two-phase system obviates the need for an ultracentrifuge and can achieve isolation efficiency at least about four times as high as that of the conventional ultracentrifugation isolation method within a very short time of about 10~20 min. Thus, the method of the present invention can greatly contribute to various diagnosis methods using extracellular vesicles, and is practical and inexpensive and thus economical and highly competitive, unlike conventional isolation methods.

Also the method of the present invention can increase the purity of extracellular vesicles contaminated with protein, enables the diagnosis of disease using the isolated extracellular vesicles, and can be applied to most fields using extracellular vesicles.

MODE FOR INVENTION

Figure 1:
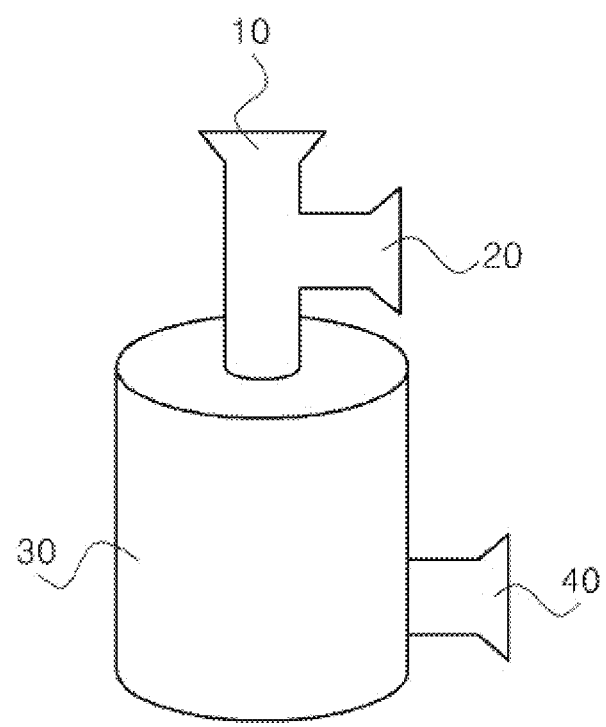
FIG. 1 schematically shows an apparatus for isolating extracellular vesicles using an aqueous two-phase system according to the present invention.

Hereinafter, a detailed description will be given of technical features of the present invention with reference to the following examples and the appended drawings. However, the examples described in the present specification are merely preferred embodiments of the present invention, and do not represent all of the technical ideas of the present invention, and thus, it is to be understood that a variety of equivalents and modifications able to substitute therefor may be provided at the point of time at which the present invention is filed. The present invention addresses a technique for isolating extracellular vesicles, in which two kinds of materials, which are immiscible with each other, are mixed with a body fluid or an aqueous solution containing extracellular vesicles to give an aqueous two-phase system, followed by isolating the extracellular vesicles concentrated at the phase boundary of the aqueous two-phase system or in one phase of the aqueous two-phase system.

In the present invention, extracellular vesicles are vesicles which are produced in cells and secreted from the cells, examples of which include, but are not limited to, exosomes, microvesicles, and microparticles.

In the present invention, a first material/a second material, which constitute the aqueous two-phase system, preferably include, but are not particularly limited to, water/EOPO (ethylene oxide propylene oxide), polyethylene glycol/dextran, polyethylene glycol/high-concentration salt, polyethylene glycol/levan, polyvinyl pyrrolidone/dextran, polyvinyl alcohol/dextran, ficoll/dextran, polyethylene glycol/poly (vinyl methyl ethyl ether), polyethylene glycol/ammonium sulfate, polyethylene glycol/sodium sulfate, polyethylene glycol/magnesium sulfate, polyethylene glycol/potassium phosphate, and polyethylene glycol/sodium carbonate.

The two materials, which are immiscible with each other and used to form the aqueous two-phase system, are more preferably polyethylene glycol/dextran, and extracellular vesicles may be characterized by being concentrated in the dextran phase, and the extracellular vesicles concentrated in the dextran phase may be isolated using a pipette, etc., but the present invention is not particularly limited thereto.

Here, polyethylene glycol has a molecular weight of 0.2~600 kDa and a concentration of 1~20 wt %, and dextran has a molecular weight of 15~2,000 kDa and a concentration of 1~20%. If the concentrations of polyethylene glycol and dextran are less than the above lower limits, an aqueous two-phase system is not formed. On the other hand, if the concentrations thereof are higher than the above upper limits, a long period of time is required to dissolve the polymers and surface tension is high between the two phases, making it difficult to dissolve a third solute such as a body fluid.

Also, when the potential of the aqueous two-phase system is adjusted through the addition of a salt, it can be confirmed that the recovery efficiency of extracellular vesicles is as high as 85% in the presence of 0.05 mol $K_3PO_4$.

The aqueous two-phase system may be subjected to centrifugation at 100~5,000×g-force for 5~15 min to thus further promote phase separation. If the centrifugation is performed at a level of less than 100×g-force, the isolation time may increase and thus the centrifugation becomes meaningless. On the other hand, even if the g-value exceeds 5,000×g-force, there is no great change in the isolation time.

In addition, according to the present invention, the purity of extracellular vesicles contaminated with protein may be increased, thus enabling various applications thereof to disease diagnosis, vaccine research and therapy, and the like. More specifically, disease may be diagnosed by isolating extracellular vesicles from the body fluid and then measuring the expression level of genes present in the extracellular vesicles.

Here, the body fluid may include, but is not particularly limited to, at least one selected from the group consisting of whole blood, serum, peritoneal fluid, breast milk, and urine. The disease may include, but is not particularly limited to, at least one selected from the group consisting of cancer, sepsis, arteriosclerosis, and rheumatoid arthritis.

The assay, such as ELISA, PCR, western blot, proteomics, or genomics, may be performed using the vesicles isolated using the aqueous two-phase system according to the present invention.

Upon measurement of the expression level of a gene present in the extracellular vesicles, the gene may be mRNA, which shows variation in expression in response to stimuli, and the process of gene separation may be the same as the conventional process for separating genetic material from cells or tissue. More specifically, the gene is synthesized into cDNA using oligo(dT), followed by real-time PCR, but the template used for the real-time PCR is not limited to cDNA.

Here, the gene includes, but is not limited to, at least one selected from the group consisting of EDN1 (Endothelin-1), VCAM1 (Vascular cell adhesion molecule 1), ICAM1 (Intercellular adhesion molecule 1), SELE (Select in E), NOS3 (Nitric oxide synthase 3), BMP4 (Bone morphogenic protein 4), VWF (Von Willebrand factor), MPZ (Myelin protein zero), IRF1 (Interferon regulatory factor 1), TNF (Tumor necrosis factor), IL32 (Interleukin 32), CFLAR (CASP8 and FADD-like apoptosis regulator), CXCL10 (Chemokine (C-X-X motif) ligand 10), IL6 (Interleukin 6), ICK (Intestinal cell (MAK-like) kinase), TFAIP2 (Tumor necrosis factor, alpha-induced protein 2), ARHGAP8 (Rho GTPase-activating protein 8), and F3 (Coagulation factor III).

According to the present invention, an apparatus for isolating extracellular vesicles using an aqueous two-phase system is illustrated in FIG. 1. More specifically, a first material and a second material for the aqueous two-phase system are introduced via an inlet 10, and a body fluid or an aqueous solution containing extracellular vesicles is fed via a feeder 20. The first material, the second material, and the body fluid or the aqueous solution containing extracellular vesicles are allowed to flow into a main body 30 connected to the inlet 10 and the feeder 20 and are thus mixed and centrifuged, thereby isolating extracellular vesicles, and the extracellular vesicles thus isolated are recovered via a collector 40.

Figure 2:
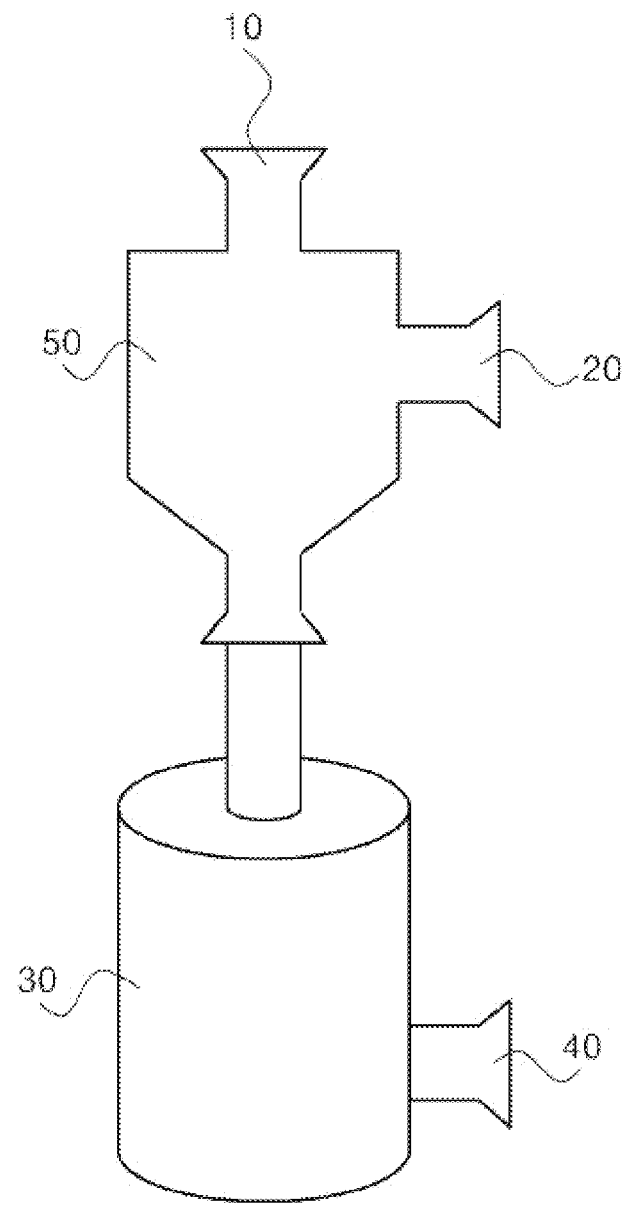
FIG. 2 schematically shows the apparatus of FIG. 1, further including a mixer.

Also, a mixer 50 may be further disposed between the inlet 10 and the feeder 20, as shown in FIG. 2, so as to facilitate the mixing of the body fluid or the aqueous solution containing extracellular vesicles with the first material and the second material, and the mixer 50 is preferably equipped with a vibrator so as to achieve efficient mixing.

Figure 3:
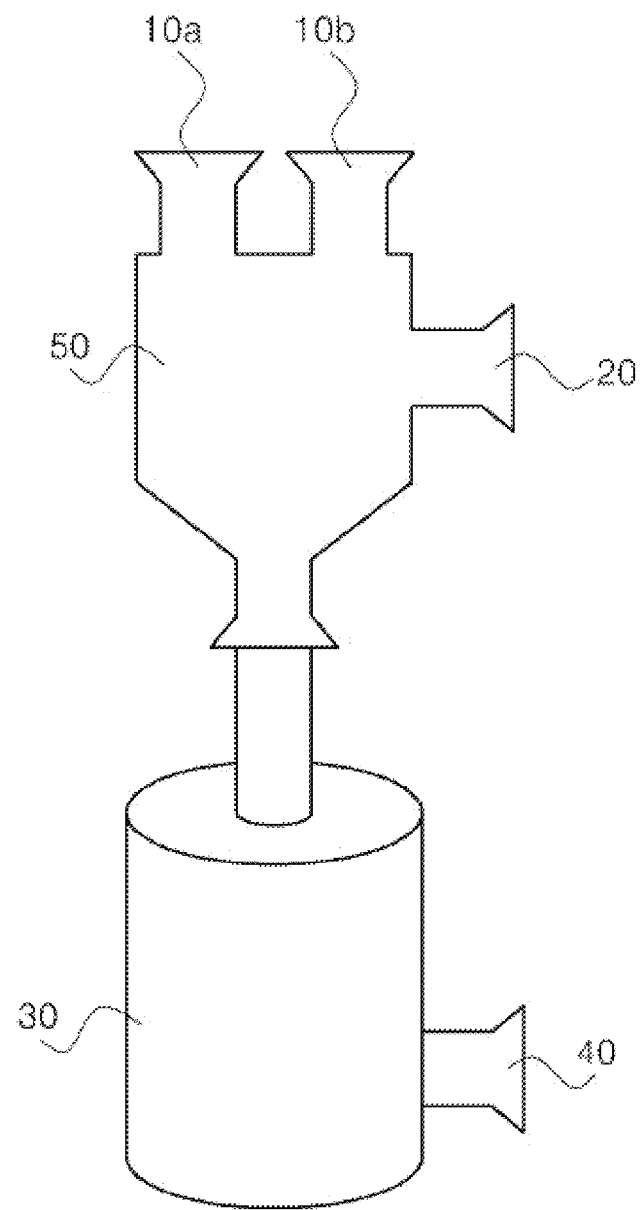
FIG. 3 schematically shows the apparatus of FIG. 2, the inlet of which is divided into two.

The inlet 10 is preferably provided in the form of a first inlet 10a and a second inlet 10b for respectively introducing the first material and the second material, as illustrated in FIG. 3, and upon the preparation of the aqueous two-phase system, the concentrations of the first material and the second material may be adjusted depending on the kinds of polymer and body fluid.

Figure 4:
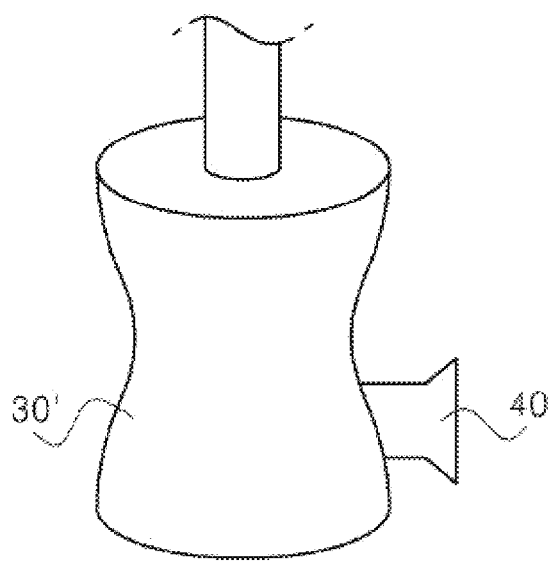
FIG. 4 schematically shows the apparatus for isolating extracellular vesicles using an aqueous two-phase system according to the present invention, in which the main body thereof is gourd-shaped.

The main body 30 may have a cylindrical shape, or may be gourd-shaped, as illustrated in FIG. 4. When the main body 30 is gourd-shaped, the phase boundary of the aqueous two-phase system is formed at the concave portion of the main body. In this case, the phase boundary is narrow and thus the trapped extracellular vesicles may be thickly formed to thereby facilitate the isolation thereof.

A better understanding of the present invention regarding the method of isolating the extracellular vesicles using the aqueous two-phase system will be given through the following examples, which are merely set forth to illustrate but do not represent all of the technical ideas of the present invention, and thus, it is to be understood that a variety of equivalents and modifications able to substitute therefor may be provided at the point of time at which the present invention is filed.

Example 1

Design of Aqueous Two-Phase System for Isolating Extracellular Vesicles

In order to find an aqueous two-phase system able to efficiently isolate extracellular vesicles, systems A, B and C, comprising polyethylene glycol/dextran aqueous solutions at different concentrations, were prepared as shown in Table 1 below.

TABLE 1

| Kind of aqueous two-phase system | Polyethylene glycol (wt %) | Dextran (wt %) |
|---|---|---|
| System A | 3.5 | 1.5 |
| System B | 7 | 3 |
| System C | 10.5 | 4.5 |

Example 2

Isolation of Extracellular Vesicles and Protein Depending on Kind of Aqueous Two-Phase System In order to evaluate the results of isolation efficiency of extracellular vesicles and protein using three kinds of aqueous two-phase systems of Example 1, 500 µl of a sample comprising extracellular vesicles and protein mixed together was added with each aqueous two-phase system of systems A, B and C of Example 1 at a desired concentration, and was then dissolved at room temperature for about 1 hr, after which the aqueous two-phase system was centrifuged at 1,000×g-force at room temperature for 10 min to induce phase separation. Here, the concentration of extracellular vesicles of the sample was 100 µg/ml and the concentration of protein thereof was 2000 µg/ml.

Thereafter, the extracellular vesicles were extracted from the phase boundary between the polyethylene glycol layer and the dextran layer, after which the concentration of the extracellular vesicles and the concentration of the protein were measured.

Figure 5:
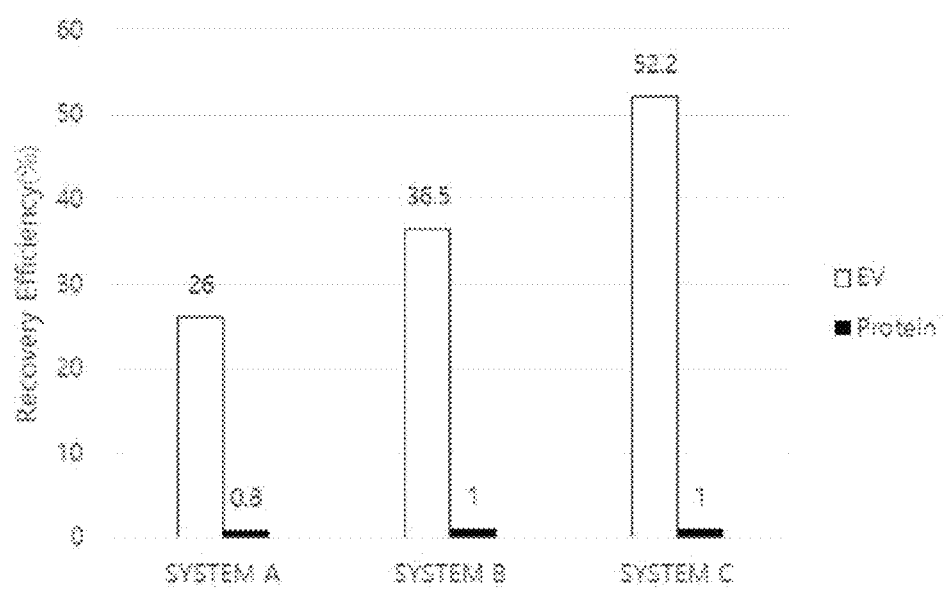
FIG. 5 is a graph showing the results of recovery efficiency of extracellular vesicles (EVs) and protein isolated using three kinds of aqueous two-phase systems (system A, system B, system C) comprising polyethylene glycol (PEG) and dextran (DEX)

In order to compare the results of isolation efficiency of extracellular vesicles in each aqueous two-phase system, the isolated amount was measured relative to the initial total amount of extracellular vesicles or protein. To this end, the percentage (%) of the amount of isolated extracellular vesicles or protein relative to the total amount is defined as recovery efficiency (E), and the recovery efficiency values using three kinds of aqueous two-phase systems were determined based on Equation (1) below. The results are shown in FIG. 5. Here, the amount of extracellular vesicles was measured from the amount of RNA and the amount of protein was determined using a Bradford assay.

Recovery efficiency($E$)=(amount of protein or extracellular vesicles isolated from dextran)/(total amount of protein or extracellular vesicles of solution)×100(%)   Equation (1)

As shown in FIG. 5, the extracellular vesicles were trapped in the largest amount when using system C, having the highest polymer concentration. The amount of trapped extracellular vesicles was 52.2% relative to the total amount. On the other hand, the protein was trapped at the phase boundary in an amount of less than 3% regardless of the polymer concentration.

These results are understood to be attributable to surface tension formed at the phase boundary of the aqueous two-phase system. By virtue of the surface tension formed at the phase boundary of the aqueous two-phase system, the particles of the aqueous two-phase system are trapped, and the trapping tendency may increase with an increase in the size of particles.

As shown in FIG. 5, since the size of extracellular vesicles is greater than the size of protein, the extracellular vesicles are greatly affected by the phase boundary. The higher the polymer concentration of the aqueous two-phase system, the stronger the surface tension. Hence, a larger amount of extracellular vesicles was trapped at the phase boundary.

Figure 6:
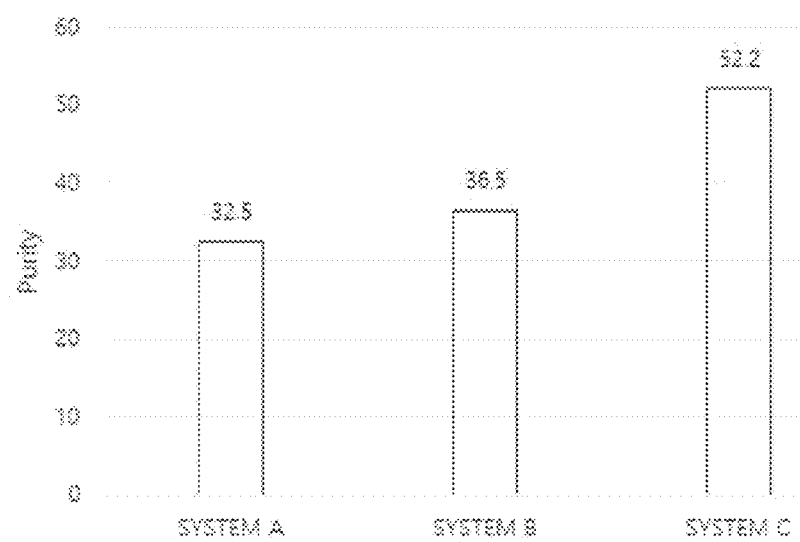
FIG. 6 is a graph showing the results of EV/protein recovery efficiency ratio using three kinds of aqueous two-phase systems.

The EV/protein recovery efficiency ratio, which is closely related to the purity of isolated extracellular vesicles, is shown in FIG. 6. The aqueous two-phase system optimal for isolating the extracellular vesicles was system C, in which the concentrations of polyethylene glycol/dextran were 10.5 wt/4.5 wt %.

Example 3

Comparison of Isolation Efficiency with Conventional Methods of Isolating Extracellular Vesicles In order to evaluate the superiority of the method of isolating extracellular vesicles using system C as the aqueous two-phase system optimal for isolating extracellular vesicles in Example 2, conventional methods of isolating extracellular vesicles, for example, ultracentrifugation isolation and commercially available ExoQuick, were applied as follows. The results are shown in FIG. 7.

When using ultracentrifugation isolation, 500 µl of a sample comprising extracellular vesicles and protein mixed together was diluted with 65 ml of phosphate-buffered saline (PBS) containing 5 mM EDTA dissolved therein and then treated at 100,000×g-force for 2 hr. Thereafter, the supernatant was removed and the amounts of precipitated extracellular vesicles and protein were measured.

When using ExoQuick, 500 µl of a sample comprising extracellular vesicles and protein mixed together was treated in accordance with the conventional method corresponding to the product protocol.

Figure 7:
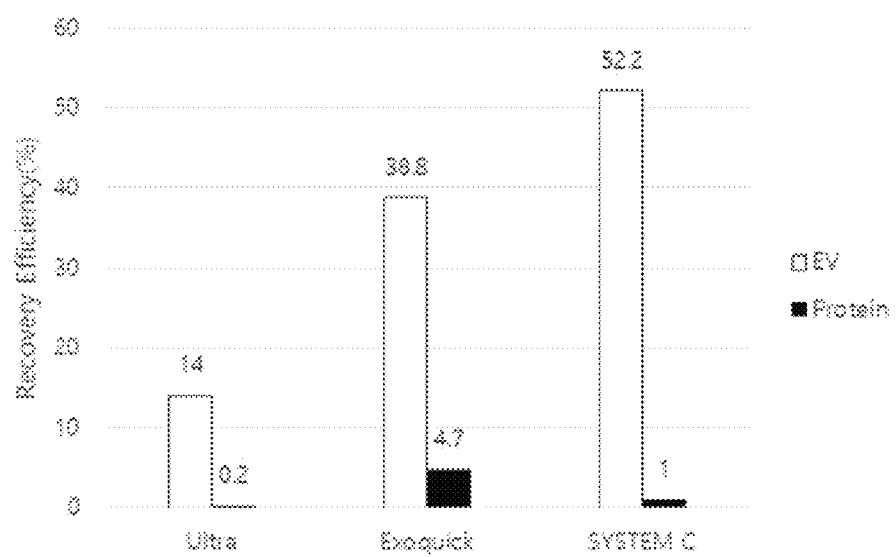
FIG. 7 is a graph showing the results of comparison of the recovery efficiency of extracellular vesicles and protein isolated according to the present invention and a conventional isolation technique.

As shown in FIG. 7, the method of the present invention using the aqueous two-phase system exhibited high isolation efficiency of extracellular vesicles compared to when using the two conventional methods, such as ultracentrifugation isolation and ExoQuick. In particular, the isolation efficiency of the invention was about four times as high as that of the ultracentrifugation isolation method.

Figure 8:
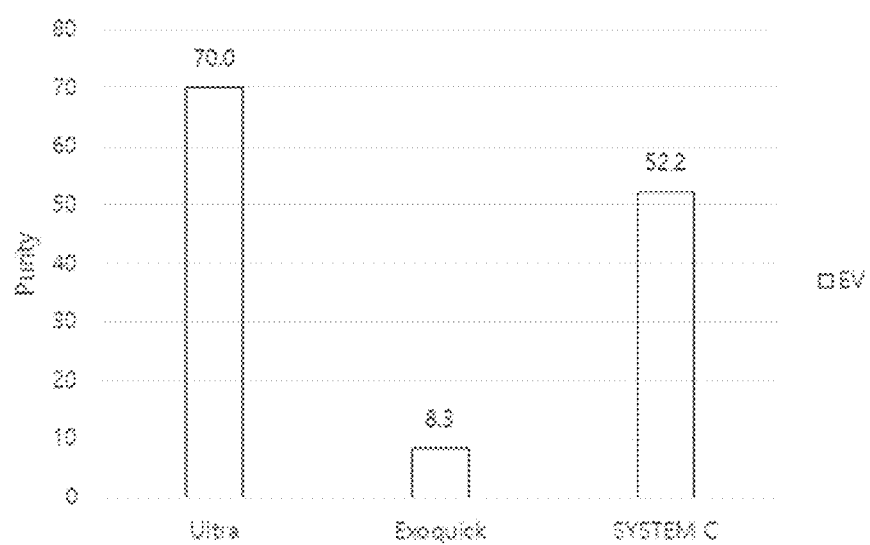
FIG. 8 is a graph showing the results of comparison of the EV/protein recovery efficiency ratio according to the present invention and the conventional isolation technique.

Moreover, in order to evaluate the purity of extracellular vesicles isolated using individual methods, the results of measurement of EV/protein recovery efficiency ratio are shown in FIG. 8. The purity of extracellular vesicles using the aqueous two-phase system was high compared to when using ExoQuick but was low compared to when using the ultracentrifugation isolation method. However, as is apparent from the results of FIG. 7, the ultracentrifugation isolation method exhibits very low isolation efficiency of extracellular vesicles. Hence, taking into consideration all of isolation efficiency and purity, the isolation of extracellular vesicles using the aqueous two-phase system according to the present invention is deemed to be the most efficient.

In order to further confirm this, western blot assay using CD81, which is a specific marker for extracellular vesicles, was performed. The results are shown in FIG. 9.

Figure 9:
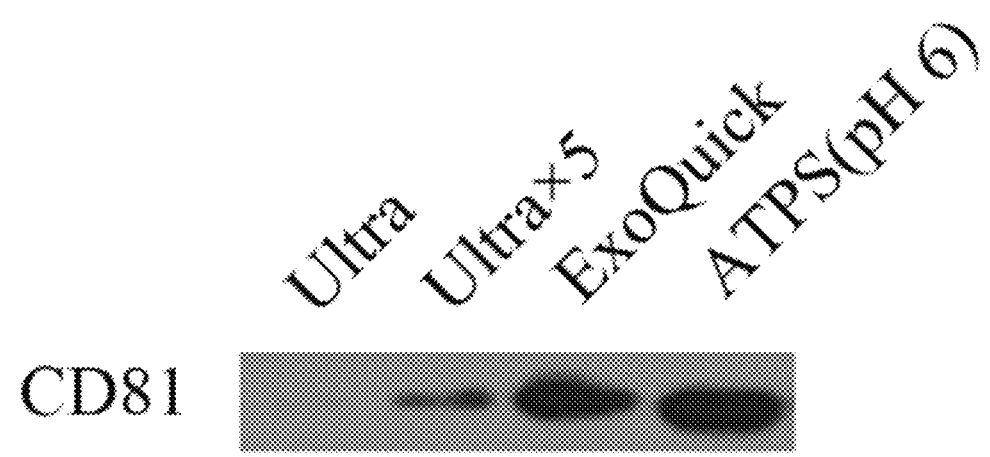
FIG. 9 shows image results of the amount of extracellular vesicles, isolated using an ultracentrifuge (Ultra), ExoQuick and an aqueous two-phase system (ATPS), using CD81, which is a specific marker for extracellular vesicles, through western blot assay (in which Ultra×5 indicates five times the amount of extracellular vesicles isolated using an ultracentrifuge)

As shown in FIG. 9, based on the results of western blot assay, the extracellular vesicles obtained using the aqueous two-phase system and those obtained using ExoQuick were represented by strong signals. In particular, the extracellular vesicles obtained using the aqueous two-phase system showed a stronger signal. However, the signal did not appear in the ultracentrifugation isolation method. The amounts of the extracellular vesicles obtained using the aqueous two-phase system and using ExoQuick were large enough for the signals to appear upon western blot assay, but the amount of the extracellular vesicles obtained using the ultracentrifuge was so small that no signal appeared upon western blot assay.

Example 4

Comparison of Methods of Isolating Extracellular Vesicles Using Aqueous Two-Phase System The method of isolating extracellular vesicles using an aqueous two-phase system according to the present invention is performed in two manners. In the first manner, the extracellular vesicles are isolated by being trapped at the phase boundary of the aqueous two-phase system (Protocol 1), and in the second manner, extracellular vesicles are isolated by being concentrated in one phase of the aqueous two-phase system (Protocol 2).

Figure 10:
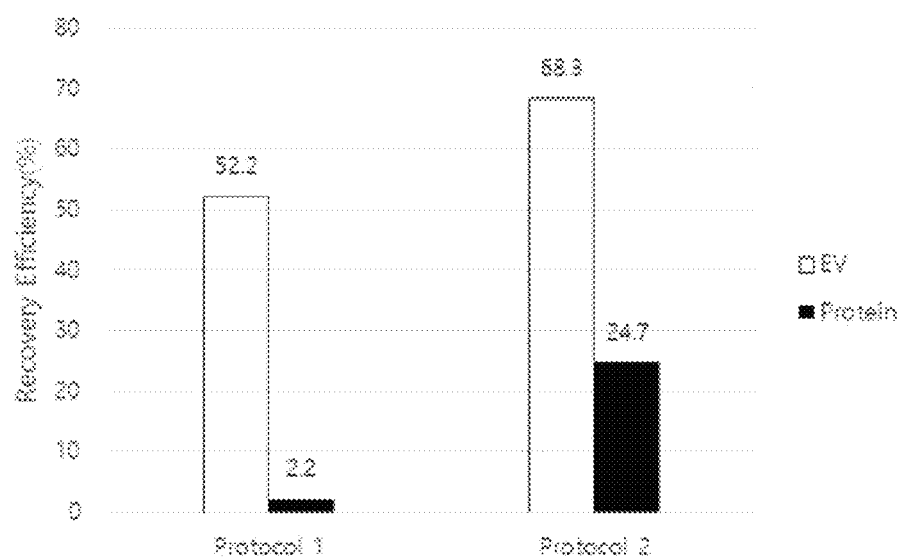
FIG. 10 is a graph showing the results when using the process of extracting extracellular vesicles from a phase boundary of the aqueous two-phase system (Protocol 1) and the process of extracting extracellular vesicles from one phase of the aqueous two-phase system (Protocol 2)

FIG. 10 shows the results of comparison of isolation efficiency in the above two manners, in which Protocol 1 is a process of extracting extracellular vesicles from the phase boundary of system C of Example 1 and Protocol 2 is a process of extracting extracellular vesicles from one phase of system A. Protocol 1 exhibits low isolation efficiency of extracellular vesicles and also low protein isolation efficiency, and Protocol 2 manifests high isolation efficiency of extracellular vesicles and also high protein isolation efficiency, and the isolation process may be selectively adopted depending on the purpose of isolation of extracellular vesicles.

When the extracellular vesicles are further added with an additive, attractive or repulsive force between molecules of the aqueous two-phase system may be controlled, thereby further increasing the isolation efficiency.

Figure 11:
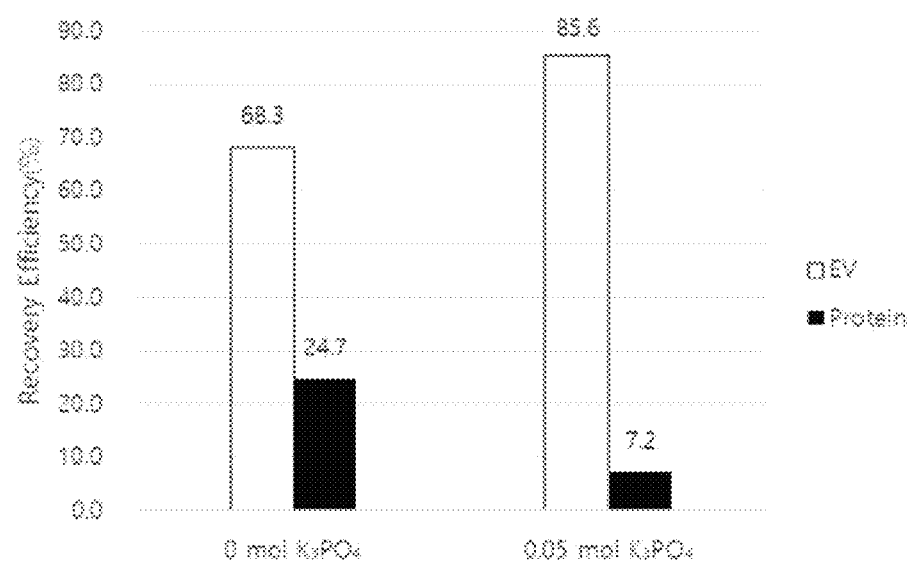
FIG. 11 is a graph showing changes in isolation efficiency and purity upon the addition of an additive in Protocol 2.

FIG. 11 shows changes in isolation efficiency by the addition of 0.05 mol $K_3PO_4$ as an additive in Protocol 2. When 0.05 mol $K_3PO_4$ is added, the isolation efficiency of extracellular vesicles is increased but the protein isolation efficiency is decreased, ultimately increasing the purity of extracellular vesicles.

Example 5

Identification of Isolated Extracellular Vesicles

In order to evaluate whether the extracellular vesicles obtained using the aqueous two-phase system are identical to the extracellular vesicles obtained using a conventional ultracentrifuge, the results of shape and RNA content of extracellular vesicles isolated using the respective methods were checked.

Figure 12:
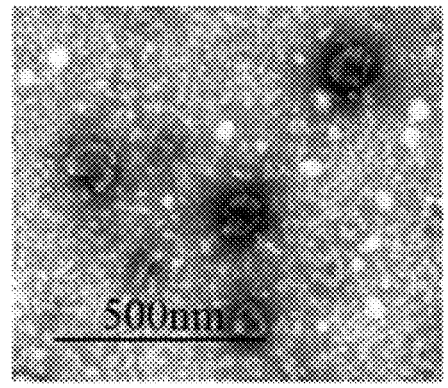
FIG. 12 shows transmission electron microscopy (TEM) images of the shapes of extracellular vesicles obtained using the ultracentrifuge and the aqueous two-phase system (ATPS)
Figure 12:
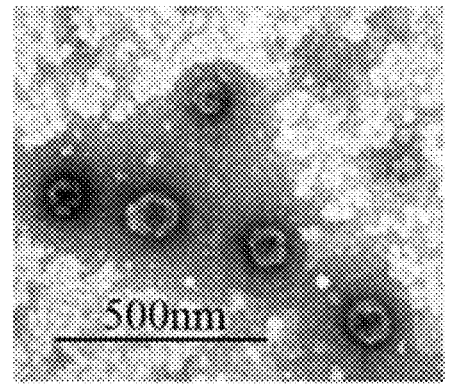

For the shape of extracellular vesicles, as shown in FIG. 12 using TEM, the shape of extracellular vesicles obtained using the ultracentrifuge was the same as that of the extracellular vesicles obtained using the aqueous two-phase system.

Figure 13:
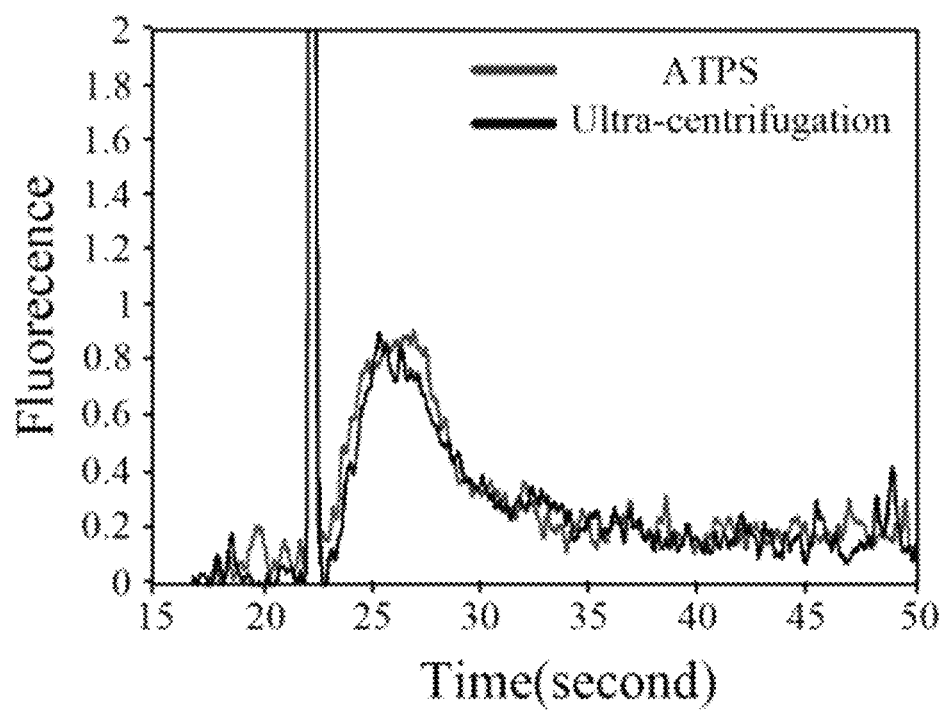
FIG. 13 shows the results of measurement of RNA profiles in extracellular vesicles obtained using the ultracentrifuge and the aqueous two-phase system.

For the RNA content of extracellular vesicles, RNA was isolated from the extracellular vesicles obtained using each of the ultracentrifuge and the aqueous two-phase system and the RNA content was analyzed using a bioanalyzer. The results are shown in FIG. 13. Here, the axis X is the time related to the size of RNA, and the axis y is the fluorescence intensity showing the relative amount of RNA depending on the size thereof.

As set forth in the results of FIG. 13, the RNA profiles in the extracellular vesicles using the ultracentrifuge were almost the same as those of the extracellular vesicles using the aqueous two-phase system, which means that the aqueous two-phase system did not damage the extracellular vesicles.

Example 6

Use for Diagnosis

The applicability of the method of isolating the extracellular vesicles using the aqueous two-phase system to the diagnosis of various diseases was confirmed as follows.

Specifically, extracellular vesicles obtained from melanoma were mixed with protein to give a sample comprising extracellular vesicles contaminated with protein, like biofluid. Thereafter, the sample comprising extracellular vesicles was isolated using an aqueous two-phase system, thereby extracting mRNA called Melan A. When the Melan A was subjected to reverse transcription PCR, as shown in FIG. 14, melanoma-related cancer could be diagnosed.

Figure 14:
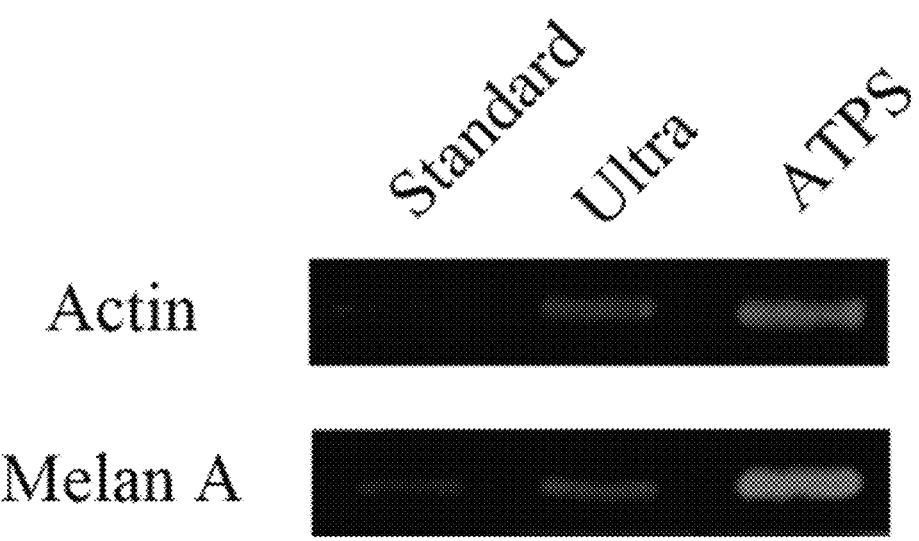
FIG. 14 shows the results after PCR of Melan A, which is mRNA of extracellular vesicles obtained using the ultracentrifuge and the aqueous two-phase system (ATPS).

As seen in FIG. 14, the PCR band of the extracellular vesicles obtained using the aqueous two-phase system was stronger than the PCR band of the extracellular vesicles obtained using the ultracentrifuge, and these results matched the results of western blot of FIG. 9.

[Description of Reference Numerals]

| | |
|---|---|
| 10: inlet | 10a: first inlet |
| 10b: second inlet | 20: feeder |
| 30: main body | 40: collector |
| 50: mixer | |

INDUSTRIAL APPLICABILITY

The present invention pertains to a method of isolating extracellular vesicles using an aqueous two-phase system, in which extracellular vesicles can be rapidly isolated at high purity from a body fluid within a short time compared to conventional techniques. In particular, the present invention discloses the use of the aqueous two-phase system, unlike the conventional techniques for isolating extracellular vesicles having problems such as low yield and impurity contamination. Hence, the aqueous two-phase system is capable of effectively separating different kinds of particles within a short time, whereby extracellular vesicles can be rapidly isolated at high yield and specificity within a short time, and thus the present invention is industrially applicable.

The invention claimed is:

1. A method of isolating extracellular vesicles using an aqueous two-phase system, comprising the steps of:
(a) preparing an aqueous two-phase system by preparing a mixture comprising a first material and a second material and then mixing the mixture with a body fluid or an aqueous solution containing extracellular vesicles; and
(b) isolating the extracellular vesicles concentrated at a phase boundary between the first material and the second material of the aqueous two-phase system or in the second material of the aqueous two-phase system without ultracentrifugation,
wherein the first material is selected from the group consisting of polyethylene glycol, polyvinyl pyrrolidone, polyvinyl alcohol, and ficoll, and the second material is dextran.

2. The method of claim 1, wherein the first material is polyethylene glycol and the polyethylene glycol has a molecular weight of 0.2~600 kDa.

3. The method of claim 1, wherein the first material is polyethylene glycol and the polyethylene glycol has a concentration of 1~20 wt %.

4. The method of claim 1, wherein the dextran has a molecular weight of 15~2,000 kDa.

5. The method of claim 1, wherein the dextran has a concentration of 1~20 wt %.

6. The method of claim 1, further comprising controlling an attractive force or a repulsive force of molecules in the aqueous two-phase system by adding an additive to the aqueous two-phase system, after the step (a).

7. The method of claim 1, further comprising pretreating the aqueous two-phase system at 100~5,000×g-force, after the step (a).

8. The method of claim 1, wherein the body fluid is at least one selected from the group consisting of whole blood, serum, peritoneal fluid, breast milk, and urine.

9. A method of increasing purity of extracellular vesicles contaminated with protein using the method of claim 1, wherein the step (a) comprises adding extracellular vesicles, which are mixed and contaminated with protein, to an aqueous two-phase system.

10. The method of claim 9, wherein the extracellular vesicles are at least one selected from the group consisting of exosomes, microvesicles, and microparticles.

\* \* \* \* \*